United States Patent [19]

Einhorn et al.

[11] Patent Number: 4,583,983
[45] Date of Patent: Apr. 22, 1986

[54] FEMALE URINARY DRAINAGE DEVICE

[76] Inventors: Carol J. Einhorn, 4740 N. Kenmore, Chicago, Ill. 60640; Joann Stegmaier, 2440 Wingren #2012, Irving, Tex. 75062

[21] Appl. No.: 545,088

[22] Filed: Oct. 25, 1983

[51] Int. Cl.$^4$ ............................................. A61F 5/44
[52] U.S. Cl. ................................... 604/329; 4/144.3
[58] Field of Search ............... 128/761; 604/327–331, 604/370; 4/144.1–144.4

[56] References Cited

U.S. PATENT DOCUMENTS

| | | | |
|---|---|---|---|
| 397,060 | 1/1889 | Knapp . | |
| 445,665 | 2/1891 | Yost . | |
| 1,497,722 | 6/1924 | Holst-Grubbe . | |
| 2,404,384 | 7/1946 | Kurkjian | 128/128 |
| 2,898,917 | 8/1959 | Wallace | 128/350 |
| 3,116,734 | 1/1964 | Terman | 128/295 |
| 3,194,238 | 7/1965 | Breece | 604/329 |
| 3,332,424 | 7/1967 | Minteer | 128/349 |
| 3,432,863 | 3/1969 | Schwartz | 4/110 |
| 3,583,388 | 6/1971 | Hovick | 128/2 |
| 3,601,125 | 8/1971 | Moss | 128/295 |
| 3,661,155 | 5/1972 | Lindan | 128/295 |
| 3,663,965 | 5/1972 | Lee, Jr. | 128/214 R |
| 3,683,914 | 8/1972 | Crowley | 128/285 |
| 3,766,920 | 10/1973 | Greene | 128/246 |
| 3,908,635 | 9/1975 | Viek | 128/2 M |
| 3,908,663 | 9/1975 | Viek | 128/349 R |
| 4,117,847 | 10/1978 | Clayton | 128/348 |
| 4,194,508 | 3/1980 | Anderson | 128/295 |
| 4,198,979 | 4/1980 | Cooney et al. | 128/295 |
| 4,233,978 | 11/1980 | Hickey | 128/293 |
| 4,270,539 | 6/1981 | Michaud | 128/295 |
| 4,341,216 | 7/1982 | Obmar | 604/370 |
| 4,421,511 | 12/1983 | Steer et al. | 4/144.3 |

FOREIGN PATENT DOCUMENTS

| | | | |
|---|---|---|---|
| 2416036 | 4/1975 | Fed. Rep. of Germany | 604/329 |
| 1216662 | 12/1970 | United Kingdom . | |

Primary Examiner—J. L. Kruter
Attorney, Agent, or Firm—Willian Brinks Olds Hofer Gilson & Lione Ltd.

[57] ABSTRACT

A noninvasive urinary drainage device is described which includes a urethral tube with a slanted upper end shaped to seal against the urethral area of a female user. This tube serves to support two stacked discs, each of which is flat, plate-like, and flexible. These two discs are configured to mechanically engage the labia minora and majora of the user. The lower end of the urethral tube is secured to a drainage tube adapted to conduct urine away from the user into a suitable receptacle. The urethral tube is held in place on the user by means of a pad which is provided with an indentation shaped to receive the larger of the two discs. This pad is formed of an absorbent material and can, for example, be held in place by means of a suitable belt. The ends of the pad are formed by an elastic net which supplies a gentle, even pressure holding the urinary drainage device in place.

14 Claims, 5 Drawing Figures

U.S. Patent    Apr. 22, 1986    4,583,983
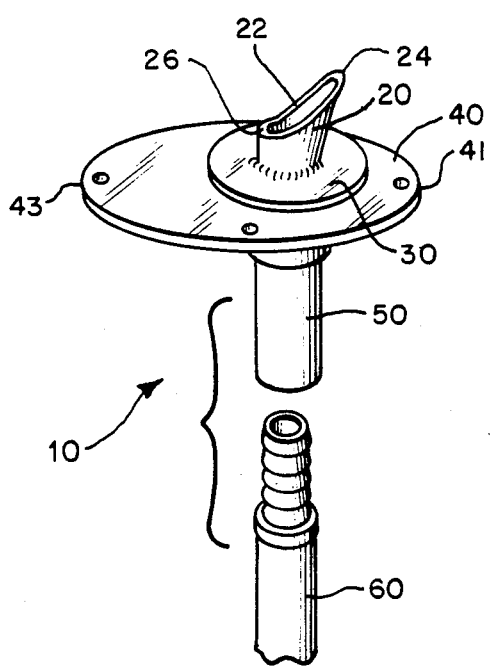
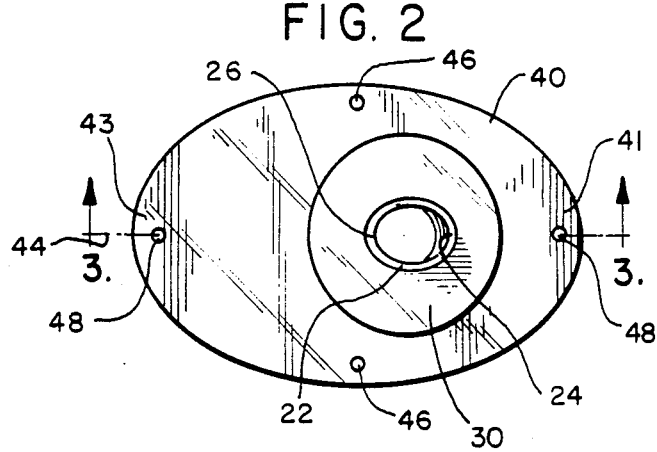
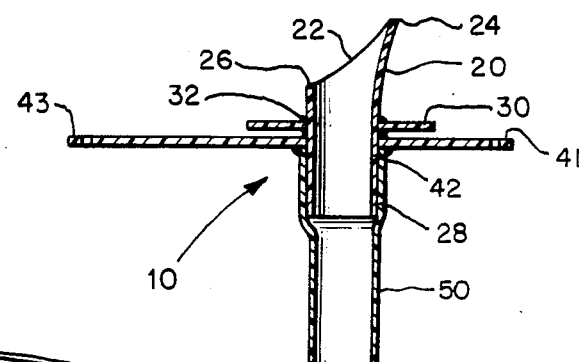
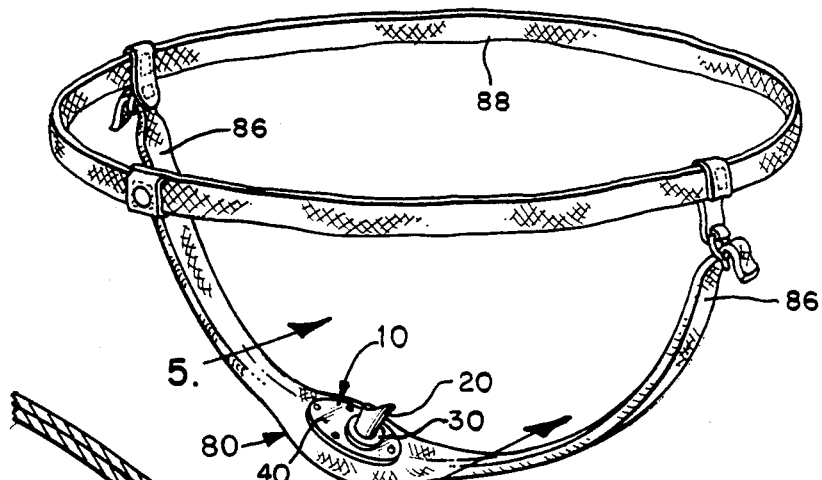
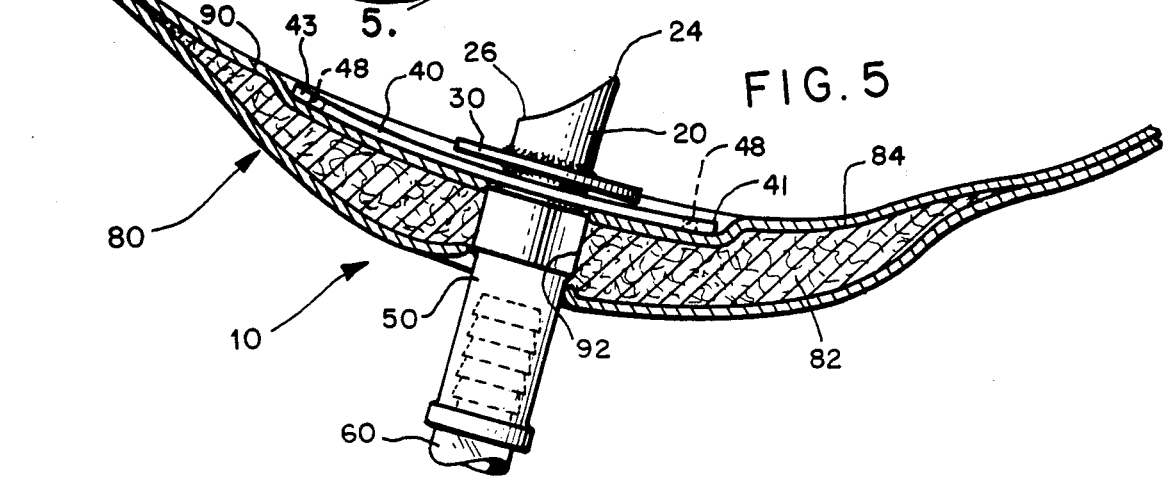

FEMALE URINARY DRAINAGE DEVICE

BACKGROUND OF THE INVENTION

The present invention relates to a non-invasive urinary drainage device for a female user suffering from incontinence or stress incontinence.

A wide variety of urinary drainage devices is known to the prior art. The devices disclosed in Breece, U.S. Pat. No. 3,194,238, Cooney, U.S. Pat. No. 4,198,979, Anderson, U.S. Pat. No. 4,194,508, Michaud, U.S. Pat. No. 4,270,539, and Moss, U.S. Pat. No. 3,601,125 disclose a number of such prior art devices. The Breece, Michaud and Moss devices are non-invasive, and are in each case held in place by means of belts.

In spite of the large amount of activity in this area, a need presently exists for an improved urinary collection device for use by female users which provides effective sealing in a simple, reliable and economical manner, and which is comfortable and nonirritating in use.

SUMMARY OF THE INVENTION

The present invention is directed to an improved urinary device which is particularly simple in construction, which operates in an effective and comfortable manner, and which minimizes problems related to contamination and infection.

According to this invention, a noninvasive urinary drainage device for a female user is provided which comprises a conforming elastomeric urethral tube having a lower end and a slanted upper end shaped to conform to and seal around the urethral region of the user. A first flat disc is formed of a conforming elastomeric material and defines a first central opening. A second oval-shaped flat disc is provided, also formed of a conforming elastomeric material, and the second disc defines a second central opening positioned in an offset manner in the second disc. The first and second discs are shaped to mechanically engage the labia minora and majora, respectively, of the user. The tube passes through the first and second openings and is secured to the first and second discs adjacent the openings. The upper end of the tube defines a posterior end and an anterior end, and the posterior end extends farther from the first disc than does the anterior end. The second opening is situated in the second disc such that the posterior end of the tube is situated nearer the perimeter of the second disc than is the anterior end of the tube. The tube and discs cooperate to hold the slanted upper end of the tube in a sealing relationship against the urethral region of the user in a noninvasive manner. A replaceable pad which is formed of an absorbent disposable material is used to secure the drainage device in place. Preferably, the pad is indented to receive the device, and the pad is formed of a stretchable material which provides a gentle, even pressure holding the device in place.

The preferred embodiment of the present invention has been found to provide a particularly effective, noninvasive urinary drainage device which is comfortable in use and simple in manufacture. This simplicity of construction results in a device which is relatively inexpensive to produce.

The invention itself, together with further objects and attendant advantages, will best be understood by reference to the following detailed description, taken in conjunction with the accompanying drawings.

BRIEF DESCRIPTION OF THE DRAWINGS

FIG. 1 is a longitudinal sectional view of a preferred embodiment of this invention.

FIG. 2 is a top view of the embodiment of FIG. 1.

FIG. 3 is a sectional view taken along line 3—3 of FIG. 2.

FIG. 4 is a perspective view of a sanitary belt and pad suitable for use in conjunction with the embodiment of FIG. 1.

FIG. 5 is a sectional view taken along line 5—5 of FIG. 4 showing the manner in which the device of FIG. 1 fits within a recess formed in the pad of FIG. 4.

DETAILED DESCRIPTION OF THE PRESENTLY PREFERRED EMBODIMENT

Turning now to the drawings, FIGS. 1-3 show three views of a presently preferred embodiment of the urinary drainage device of this invention. FIGS. 4 and 5 show the device as used with a pad and belt to hold the device in place.

In the figures, the reference numeral 10 is used to refer generally to the illustrated embodiment of this invention. This embodiment 10 is made up essentially of four parts; a urethral catheter or tube 20, a circular disc 30, an oval disc 40, and a drainage tube 50. The device is held in place as shown in FIGS. 4 and 5 by a pad 80 and a belt 88.

As best shown in FIGS. 1-3, the urethral tube 20 defines an oval-shaped slanted upper end 22 and a lower end 28. The upper end 22 is slanted as shown in FIG. 1 and it defines a posterior end 24 and an anterior end 26. The urethral tube 20 is longer at the posterior end 24 than it is at the anterior end 26. The tube 20 forms the central structural connecting member of the entire embodiment 10.

A circular, flexible disc 30 is provided which defines a central opening 32 sized to fit over an intermediate portion of the urethral tube 20. The central disc 30 is secured to the tube 20 by means of a suitable adhesive at the point where the tube 20 passes through the central opening 32. The disc 30 need not be precisely circular; its shape is selected to mechanically engage the labia minora of the user.

An oval disc 40 is also provided which defines a central opening 42 sized to fit over the urethral tube 20. As before, the oval disc 40 is secured firmly to the urethral tube 20 by means of a suitable adhesive at the point where the tube 20 passes through the opening 42. As used herein, the term "oval" is intended in its broad sense to encompass a wide range of elliptical and other elongated shapes. The disc 40 need not be shaped precisely as shown in the drawings; its shape is selected to mechanically engage the labia majora of the user.

As shown in FIGS. 1-3, the urethral tube 20 is not precisely centered in the oval disc 40. Rather, the tube 20 is offset in the oval disc 40, and is situated on a major axis 44 of the disc 40. This major axis 44 corresponds to a maximum diameter of the oval disc 40 and extends between a posterior end 41 and an anterior end 43 of the oval disc 40. The disc 40 is provided with an array of perforating holes 46,48 which extend completely through the oval disc 40 as shown in FIG. 1. It should be understood that the circular and oval discs 30,40 are both secured to the urethral tube 20, but that otherwise the two discs 30,40 are independent of one another and free to flex, fold and bend with respect to one another.

A drainage tube 50 is secured to the lower end 28 of the urethral tube 20, as for example by means of a suitable adhesive. This drainage tube 50 is adapted for connection to an extension tube 60, as for example by means of a standard connector fitting as shown in FIG. 1. In use, the extension tube is typically connected to a sealed container such as a collapsed bag. In alternate embodiments of this invention, the drainage tube 50 can be provided with an extended length, and the extension tube 60 can be entirely eliminated.

As shown in FIGS. 1-3, the circular and oval discs 30,40 are pliable, planar, and plate-like, and they are provided with parallel upper and lower surfaces which are co-extensive with the respective discs, 30,40. No ridges or rims of any type are provided, in order not to interfere with the conformability and flexibility of the discs 30,40.

Merely by way of illustration and not by way of limitation, the following details regarding materials and dimensions are provided to clarify the structure of the illustrated embodiment. In this embodiment, the urethral tube 20 has a length of 2 centimeters and a maximum width across the upper end 22 of 1.5 centimeters. The posterior end 24 extends away from the circular disc 30 by 1.5 centimeters, and the anterior end 26 extends away from the circular disc 30 by 1 centimeter. In this embodiment, the urethral tube 20 is made of a flexible, conformable, elastomeric silicone material of approximately 30 durometer.

In the illustrated embodiment, the circular disc 30 has a diameter of 2.5 centimeters and a central opening sized to fit over the tube 20. The disc 30 is approximately 3 millimeters in thickness and is formed of a semiflexible elastomeric silicone material of approximately 45 durometer.

The oval disc 40 in the illustrated embodiment has a greatest length of 7.5 centimeters, a greatest width of 4.7 centimeters, a thickness of 3 millimeters, and is formed of a flexible silicone material of approximately 30 durometer. In this embodiment the perforating holes 46,48 are ⅛th inch in diameter.

In the illustrated embodiment, the drainage tube 50 does not contact the user, and therefore can be made of a more rigid material, such as a silicone material of 160 durometer. The entire embodiment 10 should preferably be formed of sterilizable materials which can be disinfected in a simple and reliable manner.

As shown in FIGS. 4 and 5, the embodiment 10 is held in place against the body of the user by means of an indented pad 80. As shown in FIG. 5, this pad 80 is formed of a central absorbent cotton mass 82 which is surrounded by an elastic tubular mesh or net 84. This net 84 defines two ends 86 which are adapted for connection to a belt 88. The belt 88 can, for example, be a standard sanitary belt known to the art. The pad 80 defines an indentation 90 sized to receive the oval disc 40, as well as a passage 92 sized to receive the drainage tube 50. As shown in FIG. 5, in use the embodiment 10 fits within the indentation 90 formed in the pad 80 in order to position the embodiment 10 properly. The pad 80, and in particular the tubular net 84, serve to provide a gentle, even pressure to hold the embodiment 10 properly in place. If desired, the pad 80 can be impregnated with an antibacterial agent to retard infection. Preferably, both the embodiment 10 and the pad 80 are formed to avoid the rectal and vaginal areas of the user (when the anterior end 43 of the oval disc 40 is positioned anteriorly on the user) in order to avoid as much as possible contact with rectal and vaginal discharges.

In use, the illustrated embodiment has been found to provide a particularly effective urinary drainage device. The urethral tube 20 is shaped to seal against the urethral region of the user, around the urethral opening, in a reliable yet comfortable manner. The circular and oval discs 30,40 are shaped so as to mechanically engage the labia minora and majora, respectively, so as to position the urethral tube 20 properly while avoiding disadvantages related to the use of invasive catheters. The disclosed embodiment is comfortable and relatively nonirritating in use, and it minimizes infection of the type typically associated with invasive catheters. The two-point support for the pad 80 provides gentle, even pressure tending to orient the collection device properly without excessive irritation. The perforating holes 46,48 allow air circulation and ventilation, thereby minimizing skin irritation.

Furthermore, the disclosed embodiment is particularly simple to manufacture. It is formed of readily available materials, and the flat, plate-like structure of the discs 30,40 contributes to the remarkable simplicity of this embodiment. Furthermore, this embodiment is simple in structure in that the two discs 30,40 as well as the drainage tube 50 are all secured to the central urethral tube 20. The discs 30,40 are flexible and are movable independently of one another in view of their lack of interconnection except around the urethral tube 20.

The disposable pad 80 provides important advantages in that it can be replaced readily and inexpensively, without replacing the discs 30,40 or the tube 50, if it is necessary to extend wearing time of the urinary drainage device.

From the foregoing, it should be apparent that an improved urinary collection device has been described which is particularly simple in construction and effective in operation. Of course, it will be apparent to those skilled in the art that a wide range of changes and modifications can be made to the preferred embodiment described above. It is therefore intended that the foregoing detailed description be regarded as illustrative rather than limiting, and that it be understood that it is the following claims, including all equivalents, which are intended to define the scope of this invention.

We claim:

1. A urinary drainage device for a female user comprising:
    an elastomeric urethral tube having a longitudinal axis extending along the longitudinal length of the tube, a lower end and a slanted upper end shaped to conform to and seal around the urethral region of the user;
    a first flat planar disc formed of an elastomeric material, said first disc defining a first central opening and shaped to mechanically engage the labia minora of the user;
    a second oval shaped flat planar disc formed of an elastomeric material, said second disc defining a second central opening positioned in an offset manner in the second disc, said second disc defining a major and a minor axis and first and second peripheral ends on the major axis, said second opening situated nearer the first end than the second end, and said second disc shaped to mechanically engage the labia majora of the user;
    said tube disposed within the first and second openings and secured to the first and second discs adjacent the first and second openings such that the first disc overlies the second disc;

said slanted upper end of the tube defining a posterior end and an anterior end, said posterior end extending farther from the first disc in the axial direction along the axial length of the tube than the anterior end, and said tube oriented such that the posterior end of the tube is situated nearer the first end than is the anterior end of the tube;

said tube and discs cooperating to hold the slanted upper end of the tube in a sealing relationship against the urethral region of the user in a noninvasive manner;

said tube, first disc and second disc conformable to the anatomy of the user.

2. The invention of claim 1 wherein the second disc is perforated with a plurality of ventilation openings.

3. The invention of claim 1 wherein both the first and second discs are pliable and plate-like, without reinforcing ribs.

4. The invention of claim 1 wherein the tube is adhesively bonded to the first and second discs adjacent the first and second openings and the tube provides the only mechanical interconnection between the first and second discs.

5. The invention of claim 1 further comprising:

an absorbent pad which defines an indentation sized to receive the second disc, a passage within the indentation sized to receive the tube, and first and second ends adapted for connection to a sanitary belt, said pad shaped and configured to hold the first and second discs and the tube in position on the user.

6. The invention of claim 5 wherein the pad comprises:

an elongated mass of an absorbent material; and an elastic mesh tube disposed around to cover the absorbent material, said mesh tube defining the first and second ends of the pad, and effective to generate a gentle, even pressure to hold the urinary drainage device in place.

7. The invention of claim 1 wherein the tube is oval in cross-section and the posterior and anterior ends are situated at opposite ends of a major axis of the oval tube.

8. A noninvasive urinary drainage device for a female user comprising:

a resilient, elastomeric urinary catheter which terminates at one end in a slanted tip section shaped to seal around the urethral orifice of the user;

a resilient, elastomeric, substantially circular, plate-like disc secured to the catheter adjacent the tip such that the circular disc surrounds the catheter, said circular disc shaped to mechanically engage the labia minora of the user and defining upper and lower parallel, planar surfaces co-extensive with the circular disc such that the circular disc is foldable and conformable to the anatomy of the user, without reinforcing ridges;

a resilient, elastomeric, oval, plate-like disc secured to the catheter adjacent the circular disc such that the oval disc surrounds the catheter and the circular disc is interposed between the tip section and the oval disc, said oval disc positioned offset on a major axis of the oval disc and said oval disc shaped to mechanically engage the labia majora of the user, said oval disc defining upper and lower parallel, planar surfaces co-extensive with the oval disc such that the oval disc is foldable and conformable to the anatomy of the user, without reinforcing ridges;

said tip section defining a posterior end and an anterior end, said posterior end extending farther from the circular disc than the anterior end and said catheter oriented such that the posterior and anterior ends of the tube are oriented along the major axis and the posterior end is situated nearer the perimeter of the oval disc than is the anterior end;

an elongated, disposable, elastic, absorbent pad which defines an indentation sized to removably receive the oval disc, a passage within the recess positioned to receive the catheter, and first and second ends adapted for connection to a sanitary belt, said pad providing a gentle, even pressure holding the circular and oval discs in place;

said pad shaped and configured to hold the circular and oval discs in engagement with the labia minora and majora of the user, respectively, and the tip section of the catheter in sealing relationship with the urethral region of the user in a noninvasive manner.

9. The invention of claim 8 wherein the circular and oval discs are bonded to the catheter by an adhesive and the adhesive provides the only interconnection between the catheter and the circular and oval discs.

10. The invention of claim 8 wherein the pad comprises:

an elongated mass of an absorbent material; and an elastic mesh tube disposed around the absorbent material, said mesh tube defining the first and second ends of the pad.

11. The invention of claim 8 wherein the oval disc is provided with plurality of ventilation openings.

12. The invention of claim 1 wherein the first and second discs are positioned parallel to one another such that the first disc closely overlies the second disc and a substantially constant distance gap is formed therebetween, said constant distance gap extending substantially from the perimeter of the first disc to the tube.

13. The invention of claim 12 wherein the first disc is shaped to avoid the vaginal area of the user.

14. The invention of claim 1 wherein the first disc is shaped to avoid the vaginal area of the user.

* * * * *